US006902207B2

(12) United States Patent
Lickliter

(10) Patent No.: US 6,902,207 B2
(45) Date of Patent: Jun. 7, 2005

(54) SELF SEALING DISCONNECT DEVICE

(75) Inventor: Hans Lickliter, Santa Clarita, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 40 days.

(21) Appl. No.: 10/136,643

(22) Filed: May 1, 2002

(65) Prior Publication Data

US 2003/0205901 A1 Nov. 6, 2003

(51) Int. Cl.[7] .............................................. F16L 35/00
(52) U.S. Cl. ........................ 285/331; 285/3; 285/921; 29/282; 604/905
(58) Field of Search ........................... 285/3, 921, 331; 29/282; 604/905

(56) References Cited

U.S. PATENT DOCUMENTS

| 3,986,508 | A | * | 10/1976 | Barrington | ................... | 604/905 |
|---|---|---|---|---|---|---|
| 4,161,949 | A | * | 7/1979 | Thanawalla | ................. | 604/905 |
| 4,610,469 | A | * | 9/1986 | Wolff-Mooij | ............... | 604/905 |
| 5,122,123 | A | * | 6/1992 | Vaillancourt | ................ | 604/905 |
| 5,330,448 | A | | 7/1994 | Chu | | |
| 5,492,147 | A | * | 2/1996 | Challender et al. | ......... | 604/905 |
| 5,514,117 | A | | 5/1996 | Lynn | | |
| 5,536,262 | A | * | 7/1996 | Velasquez | ................... | 604/905 |
| 5,815,182 | A | * | 9/1998 | Otis et al. | .................... | 604/905 |
| 6,189,859 | B1 | * | 2/2001 | Rohrbough et al. | ........ | 604/905 |
| 6,234,538 | B1 | * | 5/2001 | Lauer | ........................ | 604/905 |
| 6,394,992 | B1 | * | 5/2002 | Sjoholm | .................... | 604/411 |

FOREIGN PATENT DOCUMENTS

| EP | 0 230 864 | 8/1987 |
|---|---|---|
| FR | 2 685 209 | 6/1993 |

* cited by examiner

*Primary Examiner*—David Bochna
(74) *Attorney, Agent, or Firm*—Gates & Cooper LLP

(57) ABSTRACT

Apparatuses and methods for connecting and disconnected fluid conduits (e.g. medical tubing) are disclosed. Typical embodiments of the Apparatuses and methods disclosed herein operate with two separate components, the first having a moveable septum and the second having a fixed septum. When the components are engaged, the device allows the flow of fluid through a conduit to which they are coupled. When the components are uncoupled, the device prevents the flow of fluid through the conduit. An exemplary embodiment of the invention includes a housing, a moveable septum slideably coupled with the housing to be alternately disposed in at least a first and second position and a piercing member having a passage for conducting fluid. The moveable septum closes the passage in the first position and is penetrated by the piercing member to open the passage in the second position.

51 Claims, 7 Drawing Sheets

SELF SEALING DISCONNECT DEVICE

BACKGROUND OF THE INVENTION

1. Field of the Invention

This invention relates generally to devices and methods for coupling and uncoupling fluid conduits. More specifically, this invention relates to fluid couplings that are employed with fluid conduits used to convey medications.

2. Description of the Related Art

Fluid couplings allow fluid conduits (e.g. medical tubing) to be conveniently coupled and uncoupled. There are many different applications for fluid couplings depending upon the type of fluids to be conveyed as well as the amount of fluid flow required.

In the medical field, devices which couple fluid conduits such as medical tubing (i.e. fluid couplings) facilitate the administration of fluid medications. For example, in delivering fluid medications such as insulin from an infusion device, fluid couplings are typically used to connect the infusion device to an infusion set that delivers the medication to the infusion site in the user's body. Fluid couplings are also used in a variety of other contexts such as to facilitate the delivery of medication and other fluids to patients through intravenous (IV) solution delivery systems. In addition, fluid couplings are used in conjunction with syringes, catheters and other medical devices that are designed to facilitate and manipulate fluid flow.

In treatment regimes for certain pathologies such as diabetes, patients may be connected to medication delivery devices such as infusion pumps for long periods of time. In these regimes, it is important that a patient have the ability to temporarily disconnect themselves from such devices in order to maintain an active lifestyle. While existing fluid couplings can be used to accomplish this, those known in the art are often are tedious to operate and can require replacement after each use. Moreover, some existing fluid couplings require cumbersome separate caps and/or valves to prevent leakage when they are disconnected.

In addition, due to the risk of infection, sterility is a significant concern with most medical devices. With blood borne disease, it is particularly important to minimize or eliminate the risk of blood contamination to patients as well as care givers. In this context, typical fluid couplings utilize piercing members such as hollow needle structures to administer medication, a design which increases the risk of exposure to pathogens. Consequently, medical devices are preferably designed to minimize the risk of needle contamination and inadvertent needle sticks to patients and their caregivers.

In view of the foregoing, there is a need in the art for self-sealing disconnect devices that are quick and convenient to operate. In addition, such devices should be designed for maximal safety and sterility. Preferably such devices are inexpensive, reusable and disposable.

SUMMARY OF THE INVENTION

Embodiments of the invention provide a self sealing disconnect device for use with fluid conduits, such as medical infusion lines. These self sealing disconnect devices allow a user to temporarily disconnect themselves from a medical device such as a medication infusion pump. Embodiments of the invention also include methods of using such devices.

Typical embodiments of the self sealing disconnect devices disclosed herein operate with two separate components, the first having a moveable septum (the "moveable septum component") and the second having a fixed septum (the "fixed septum component"). When the components are engaged, the device allows the flow of fluid through a conduit to which they are coupled. When the components are uncoupled, the device prevents the flow of fluid through the conduit.

In preferred embodiments of the moveable septum component, the moveable septum is movable and slides along the length of a fluid conduit. Generally the section of the fluid conduit used with this component is a hollow piercing member such as a needle. In this component, the moveable septum component can automatically seal the fluid conduit when a user disconnects one portion of a fluid conduit system from another. Automatic sealing of the device eliminates the need for a user to seal the device with a separate plug or other component upon disconnection. In addition, in such designs a fluid conduit piercing member is embedded within the moveable septum component to avoid exposing the piercing member to a user and to prevent contamination of the piercing member during disconnected periods.

Embodiments of a moveable septum component include a housing and a moveable septum slideably coupled with the housing to be alternately disposed in at least a first and a second position. Typically the moveable septum closes a passage in a fluid conducting hollow piercing member in the first position and is penetrated by the piercing member to open the passage in the second position. A carrier can also be used to hold the moveable septum slideably coupled with the housing. In addition, the housing can also include a stop to retain the moveable septum as a slideable coupling with the housing.

In some embodiments of the invention, at least one retention feature is coupled to the moveable septum and adapted to engage a mating retention feature of a fixed septum component. The retention feature is adapted to position the moveable septum in the first position before the fixed septum component is uncoupled from the piercing member. An illustrative retention feature is a snap fitting. In addition, the retention feature can be constructed integral to the moveable septum or disposed on a separate moveable septum carrier. Further, the housing of the movable septum component can also include a housing engagement feature for secure coupling to the fixed septum component.

Embodiments of a fixed septum component that engage the moveable septum component include a fixed septum that is pierced by the piercing member when the fixed septum component is coupled with the moveable septum component and the moveable septum is in the second position. For example, a fixed septum component embodiment of the invention includes a housing, a septum fixed to the housing and at least one retention feature coupleable to a moveable septum component. The fixed septum is pierced by a piercing member of the moveable septum component and a passage for fluid on the piercing member is opened when the retention feature is coupled to the moveable septum component in the second position.

Preferred retention features are typically adapted to position the moveable septum in the first position before the retention feature is uncoupled. The retention feature can be a snap fitting integral to the fixed septum or the housing. The housing can also include a housing engagement feature to engage the moveable septum component.

In preferred embodiments of the invention, the piercing member is fixed to the housing of the moveable septum component. Alternatively it can be disposed on a separate component. The fluid conducting passage of the piercing member can include a radial and/or axial opening. In addition, the structure of piercing member can be manipulated according to the specific fluid conduit system in which the apparatus disclosed herein is employed (e.g., can be sharp or blunted, etc.).

An exemplary fluid coupling system of the self sealing disconnect device includes a moveable septum component and a fixed septum component. The moveable septum component includes a first housing and a moveable septum slideably coupled with the first housing to be alternately disposed in at least a first position where the moveable septum closes a passage in a piercing member for conducting fluid and a second position in which the moveable septum is penetrated by the piercing member to open the passage. The fixed septum component includes a second housing coupleable to the moveable septum component and a septum fixed to the second housing. The fixed septum is pierced by the piercing member and the passage is opened to allow fluid flow when the fixed septum component and the moveable septum component are coupled with the moveable septum in the second position.

BRIEF DESCRIPTION OF THE DRAWINGS

Referring now to the drawings in which like reference numbers represent corresponding parts throughout.

DETAILED DESCRIPTION OF THE PREFERRED EMBODIMENT

1. Overview

As described above, the self sealing disconnect devices of the present invention can operate as two components, a moveable septum component and a fixed septum component, each having a septum. In the fixed septum component, the septum is held in a fixed position. In the moveable septum component, the septum is movable and slides along the length of a fluid conduit that pierces this septum (e.g. a needle or other piercing member).

Generally, embodiments of the invention use a piercing member (such as a needle) that is protected to eliminate the potential of hazardous needle exposure to the user. The fluid conduit of the coupling is also sealed automatically whenever the coupling is separated. Thus, the user is not required to seal the coupling with a "plug" or other device upon disconnection. In addition, automatic sealing prevents contamination of the piercing member during disconnected periods.

In the "closed" position, an opening of the piercing member is sealed by the moveable septum. The septum sealed opening of the piercing member can be disposed at the end (e.g., an axial opening see FIGS. 3A and C) or the side (e.g., a radial opening see FIG. 3B) of the piercing member. The only requirement is for the opening to be sealed by the moveable septum when the opening is embedded in the moveable septum.

To couple the components and open the fluid path, the fixed septum component is engaged with the moveable septum component. In doing so, the fixed-septum coupling forces the moveable septum back until both septums are penetrated by the piercing member to establish fluid flow.

During the coupling, a feature on the fixed septum component can engage the moveable septum (and/or a moveable septum carrier). These features provide retentive characteristics so that when the two components are disconnected, the moveable septum is positioned to seal the opening in the piercing member automatically without additional user steps. A stop feature on the moveable septum component can prevent the moveable septum from being pulled out of the moveable septum component when the fixed septum component is withdrawn.

2. Exemplary Embodiments

Figure 1A:
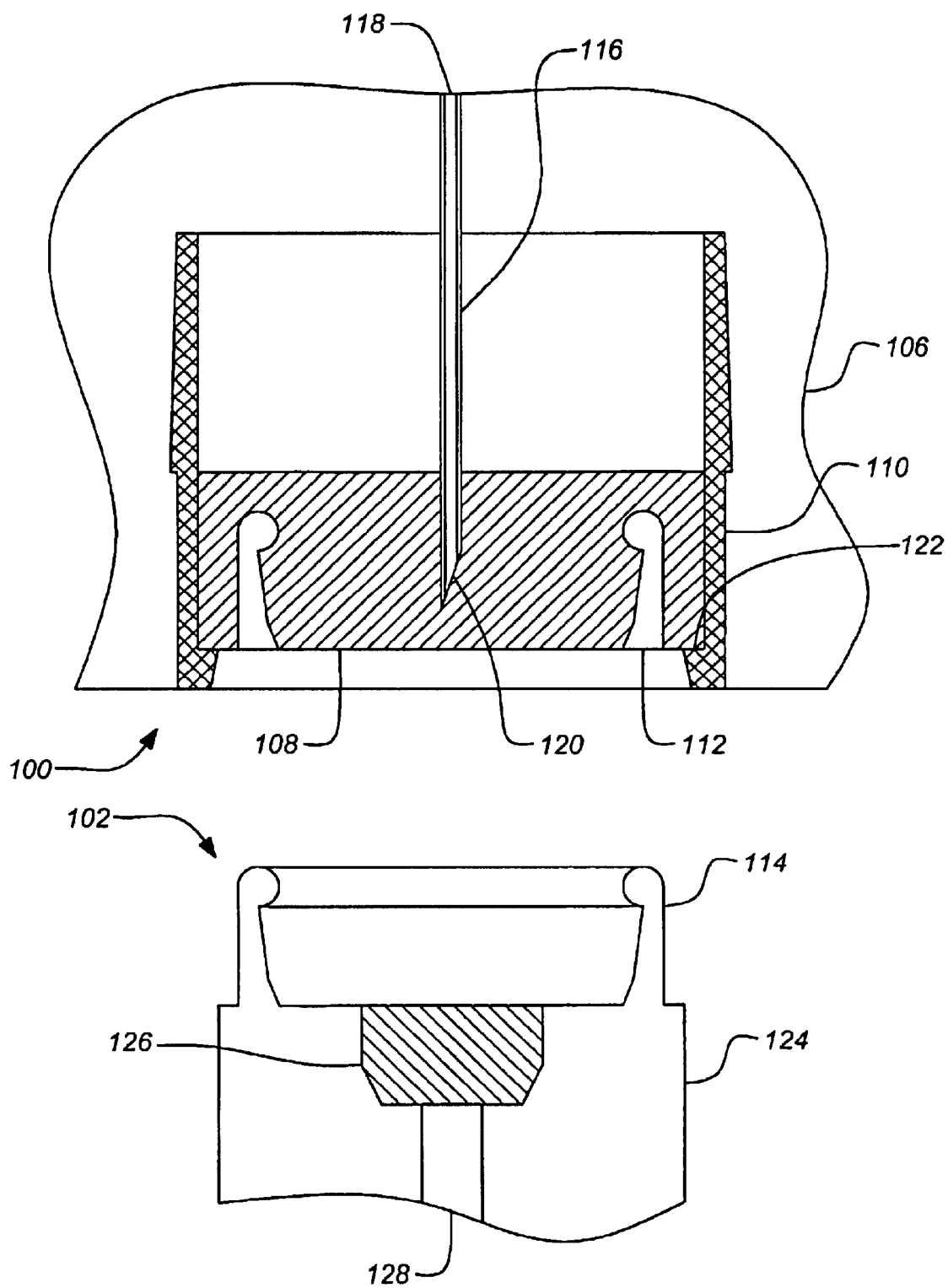
FIGS. 1A and 1B illustrate a cross-section view of exemplary embodiments of the invention including a moveable septum component and matching fixed septum component.
Figure 1B:
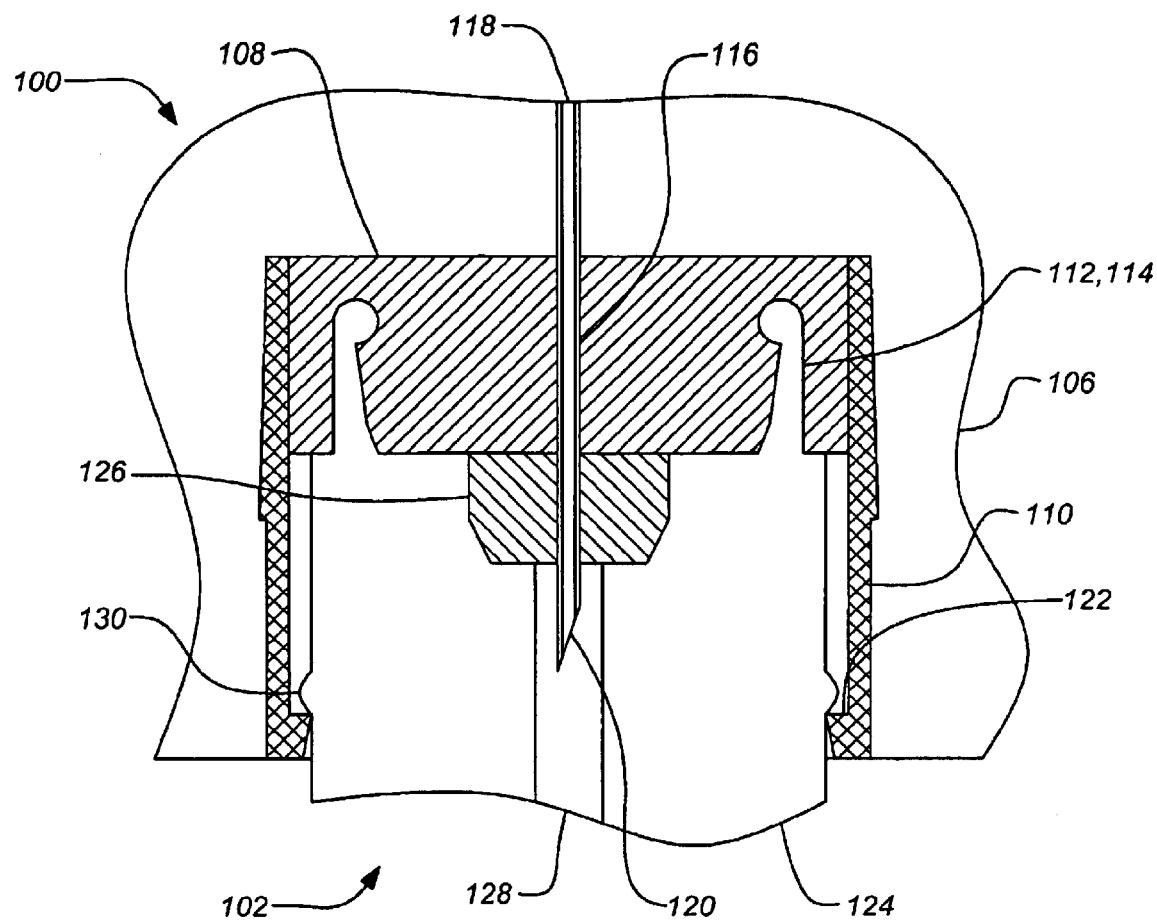

FIGS. 1A and 1B illustrate a cross-section view of exemplary embodiments of the invention including a moveable septum component 100 and matching fixed septum component 102. Typically the two components are substantially cylindrical and designed to operate together to open a fluid flow path when they are coupled and automatically close the fluid flow path as they are uncoupled. When separated, the components 100 and 102 are each automatically sealed from leaking. In alternative embodiments, shapes other than cylindrical (i.e., circular cross-sections), such as, but not limited to, square, rectangular, triangular, polygonal, oval, or the like, may be used.

The moveable septum component 100 typically includes a housing 106 and a moveable septum 108 coupled together so that the septum 108 slides axially within the housing 106. An optional separate sleeve 110 can be attached to the housing 106 to guide the moveable septum 108 and facilitate simpler manufacturing and assembly. The moveable septum 108 can include a retention feature 112 that engages a matching retention feature 114 on the fixed septum component 102.

A piercing member 116 can be axially disposed in the housing 106 along a line parallel to the sliding direction of the moveable septum 108. The piercing member 116 can provide a fluid passage 118 for conducting fluid through the two components when they are joined. At least one opening 120 can be formed in the piercing member 116 near the piercing end to provide a flow path when the two components 100 and 102 are coupled.

Typically the housing 124 of the matching fixed septum component 102 carries a fixed septum 126 that closes a fluid passage 128. The fluid passage 128 conveys fluid when the components 100 and 102 are coupled. The housing 124 can also include the matching retention feature 114 designed to engage the feature 112 on the moveable septum component 100.

FIG. 1A illustrates the moveable septum component 100 and matching fixed septum component 102 in an uncoupled condition. When the moveable septum component 100 is uncoupled, the moveable septum 108 is positioned to seal the opening 120 in the piercing member 116. Thus, no fluid leaks from the moveable septum component 100 when it is uncoupled from the fixed septum component 102. A stop 122, such as a lip, bump, ridge, or the like, on the sleeve 110, holds the moveable septum 108 in the proper position to close the opening 120 of the piercing member 116 and prevents the moveable septum 108 from being drawn out of the housing 106 when the two components 100 and 102 are uncoupled as described below.

As the moveable septum component 100 and matching fixed septum component 102 are coupled, the two components are brought together to engage the retention features 112, 114. At this point, the moveable and fixed septums 108, 126 are brought into contact with each other. As the components 100 and 102 are pressed together, the housing 124 and/or septum 126 of the fixed septum component 102 pushes the moveable septum 108 into the housing 106 and forces the piercing member 116 through the contacting septums 108, 126. During the coupling process, the engaged retention features 112, 114 may serve to aid in guiding the two components 100 and 102 together. Engagement of the retention features 112, 114 prepares the components 100 and 102 for automatically sealing the fluid path when the components are uncoupled.

FIG. 1B illustrates the moveable septum component 100 and matching fixed septum component 102 in a coupled condition. In this position, the piercing member 116 is driven through both septums 108, 126 to connect the fluid passages 118, 128 and allow a fluid flow through the coupled components 100 and 102.

In addition, the moveable septum component 100 and fixed septum component 102 can incorporate a housing engagement feature that allows the two components 100 and 102 to be secured in the coupled position. For example, as depicted in FIG. 1B, the housing 124 of the fixed septum component 102 includes a ridge engagement feature 130 that snaps into the housing 106 (or sleeve 110) of the moveable septum component 100. In this example, the engagement feature 130 snaps past the stop 122. In this manner, the feature 130 provides additional resistance to prevent the two components 100 and 102 from slipping apart but only engages when they are fully coupled and the fluid path is opened.

When the moveable septum component 100 and matching fixed septum component 102 are uncoupled, the engaged retention features 112, 114 enable the fixed septum component 102 to draw the moveable septum 108 back to the closed position (as shown in FIG. 1A). The stop 122 then holds the moveable septum 108 with enough force to disengage the retention features 112, 114 and prevent the moveable septum 108 from being pulled out of the housing 106.

The retention features 112, 114 are depicted as an annular snap fitting. Ideally, the features 112, 114 should engage with a resistive force lower than the combination of drag forces on the moveable septum 108 from the piercing member 116 and the housing 106 (or sleeve 110). This will insure that moveable septum 108 and the fixed septum 126 are in contact before the piercing member 116 erupts through the moveable septum. Also, the retention features 112, 114 should disengage with a resistive force higher than the combination of drag forces on the moveable septum 108 from the piercing member 116 and the housing 106 (or sleeve 110).

The snap fitting retention features 112, 114 enable a very simple single motion coupling process. Many other suitable configurations are possible, however. For example, the annular snap fitting can be segmented and/or limited to engaging posts and sockets. In addition, more complex retention features are also possible. For example, a twist-lock and/or threaded retention feature (not shown) can be used which would require the user to twist the components together to engage and disengage the fixed septum component. Retention feature configurations of this type may require a keyway or some other asymmetric engagement feature to prevent the moveable septum from rotating about the sliding axis as the components are twisted together.

In addition, some portion of the apparatus (e.g. the region behind the moveable septum) can be ventilated to vent resistive air pressure that may occur against the moveable septum 108 and facilitate the engagement and disengagement of the components. Ventilation can be made through the moveable septum 108 and/or the housing 106 and sleeve 110.

The housings 106, 124 of either component can have sockets or nipple fittings for connection to fluid conduit, such as medical tubing. Alternately, a fluid conduit can be fixed to either coupling component. For example, one component (either the moveable septum component 100 or the fixed septum component 102) can be made integral to an infusion site or reservoir for use with an infusion device.

Furthermore, the various parts of the components can be manufactured from rigid plastics, such as modified polycarbonate or PVC, or other suitable materials known to those skilled in the art. The septums 108 can be made from silicone rubber to facilitate many repeated cycles or from a butyl rubber for a more limited number of uses or combinations of materials. Furthermore, the septums 108 can be held in place by any suitable means, such as swaging or bonding or a retention ring. The piercing member 116 can be bonded or insert-molded into the moveable septum component housing 106. The moveable septum 108 can also be lubricated to move more freely in the housing 106.

Figure 2A:
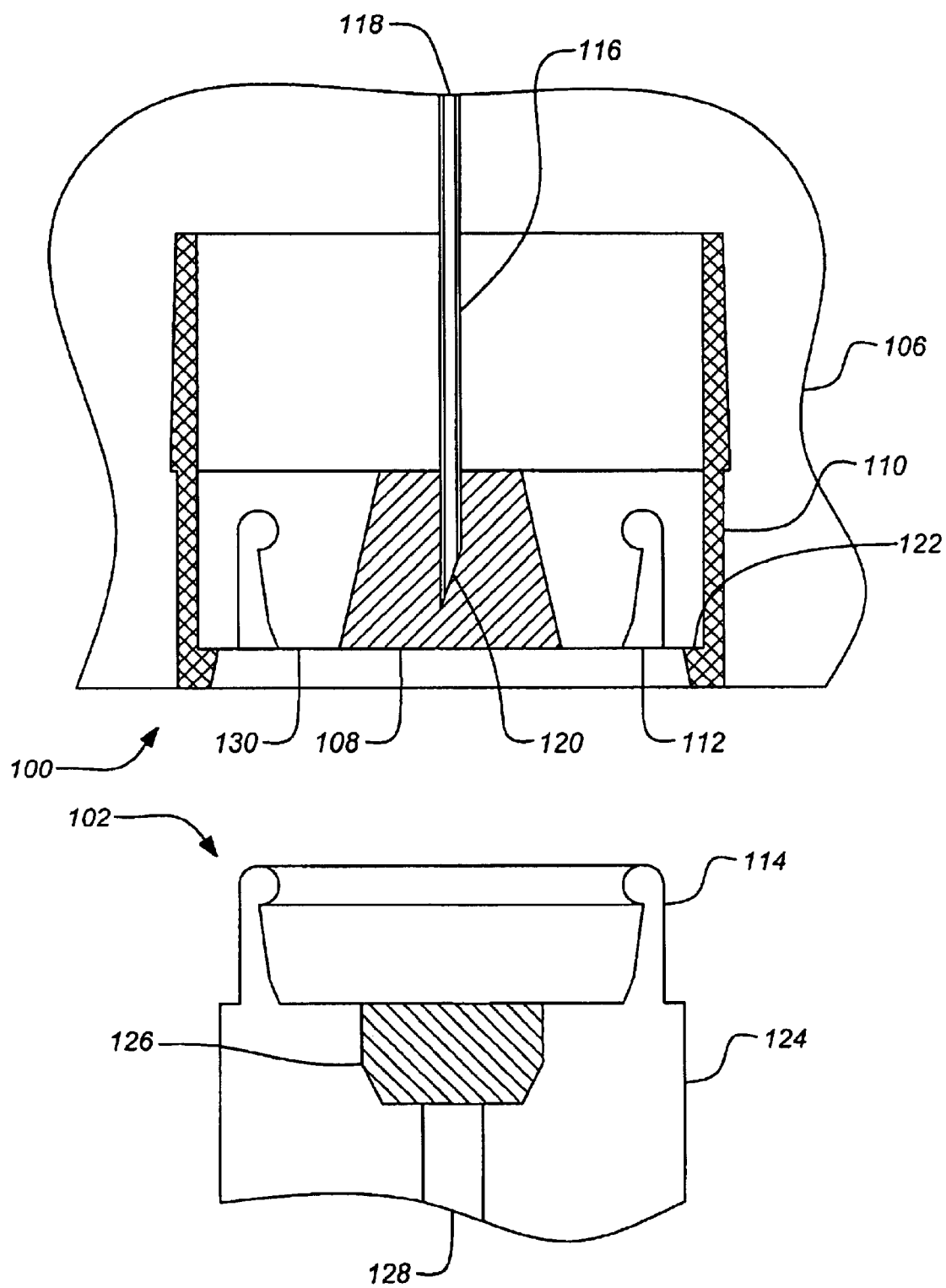
FIGS. 2A and 2B illustrate a cross-section view of additional exemplary embodiments of the invention including a moveable septum component and matching fixed septum component.
Figure 2B:
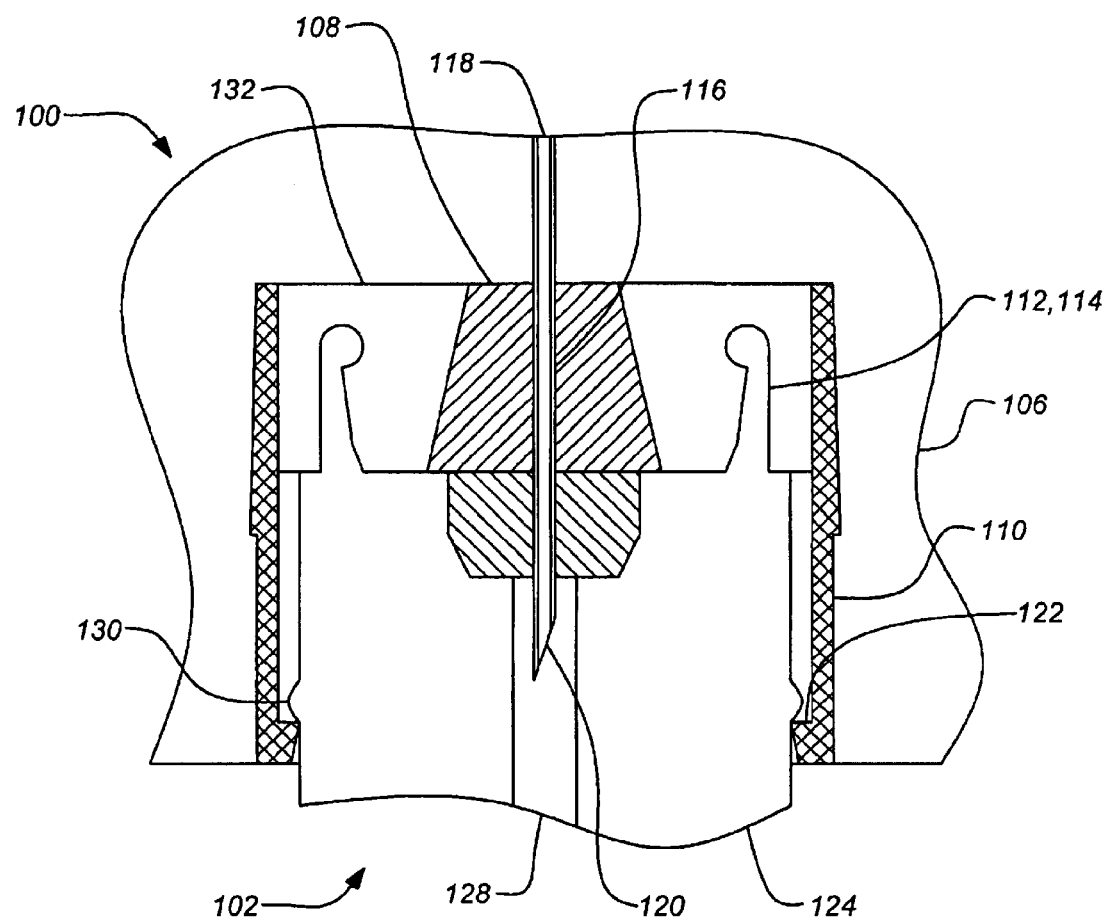

FIGS. 2A and 2B illustrate a cross-section view of additional exemplary embodiments of the invention including a moveable septum component and matching fixed septum component. These embodiments of the invention operate in the same manner as the embodiments previously described, however in this embodiment the moveable septum 108 is held in a distinct carrier 132. The carrier 132 serves to reduce friction reacted between the moveable septum 108 and the housing 106 or sleeve 110 without additional lubrication. In this embodiment, the moveable septum 108, can be pressed, sealed, or snapped into the low friction carrier 132, which can be made from polypropylene. Ventilation to the chamber behind the moveable septum 108 can be provided through the carrier 132.

Figure 3A:
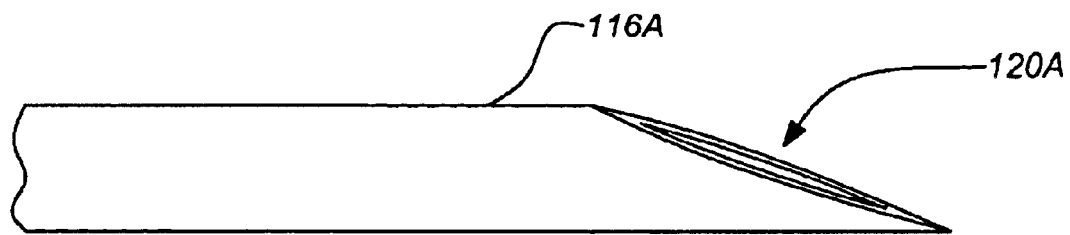
FIGS. 3A–3C illustrate some exemplary openings in the piercing member.
Figure 3B:
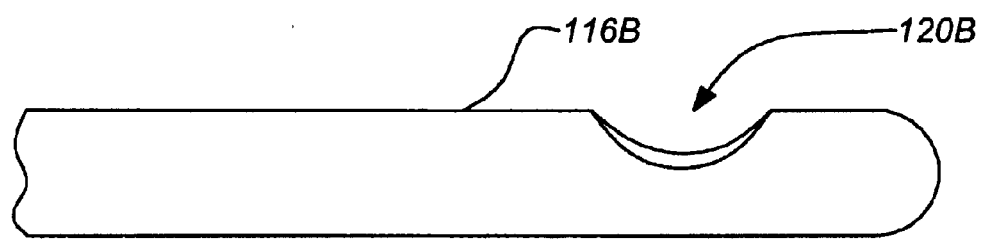
Figure 3C:
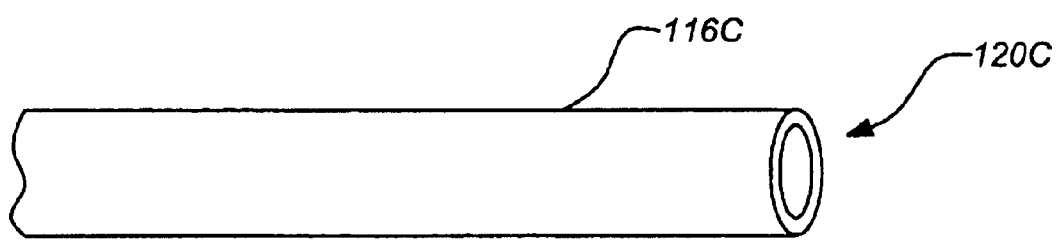

FIGS. 3A–3C illustrate exemplary embodiments of the piercing member 116. The piercing member 116 can also be implemented with the opening 120 in many alternate configurations. The principle requirement is that the opening 120 is effectively sealed with the moveable septum 108 in the closed position. For example, FIG. 3A depicts a typical piercing member 116A with a sharp tip formed from a single angled planar cut to create an axial opening 120A at the end of the piercing member. A sharp tip is easily manufactured and able to penetrate the septums minimizing coupling resistance.

FIG. 3B depicts a piercing member 116B with a blunt tip and a radial (or side) opening 120B. This piercing member improves the safety of the device as the exposed tip cannot easily pierce a user's skin. In addition, it may be more easily sealed as the radial opening is directed to the wall of the pierced septum. However, it may also be more difficult to manufacture and provides greater resistance in use than the embodiment of FIG. 3A.

FIG. 3C depicts a piercing member 116C with a blunt tip and an axial opening 120C formed from a single perpendicular planar cut. This embodiment is easily manufactured (like the embodiment of FIG. 3A), however, it is more likely to provide greater resistance and/or leakage in operation.

Many other suitable configurations can be formed with one or more radial and/or axial openings 120 in the piercing member 116 combining the elements described in the embodiments shown in FIGS. 3A–3C.

3. Exemplary Methods of Connecting Fluid Conduits

Figure 4A:
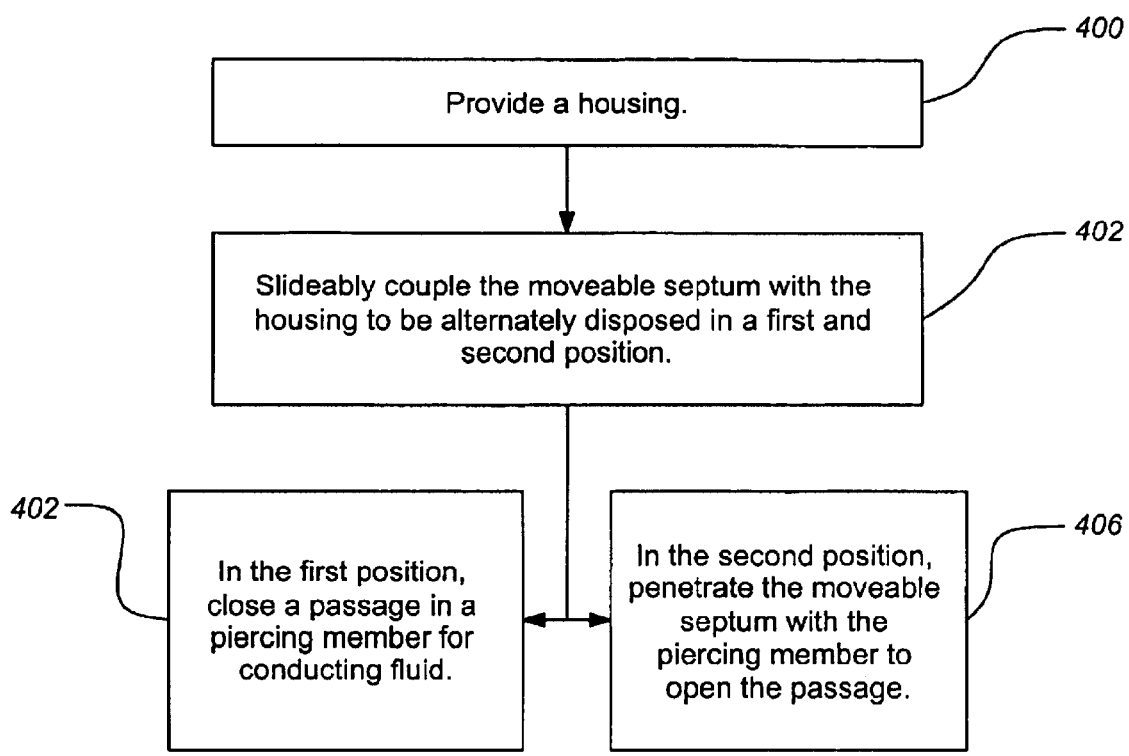
FIGS. 4A and 4B are flowcharts of exemplary methods of fixed septum component.
Figure 4B:
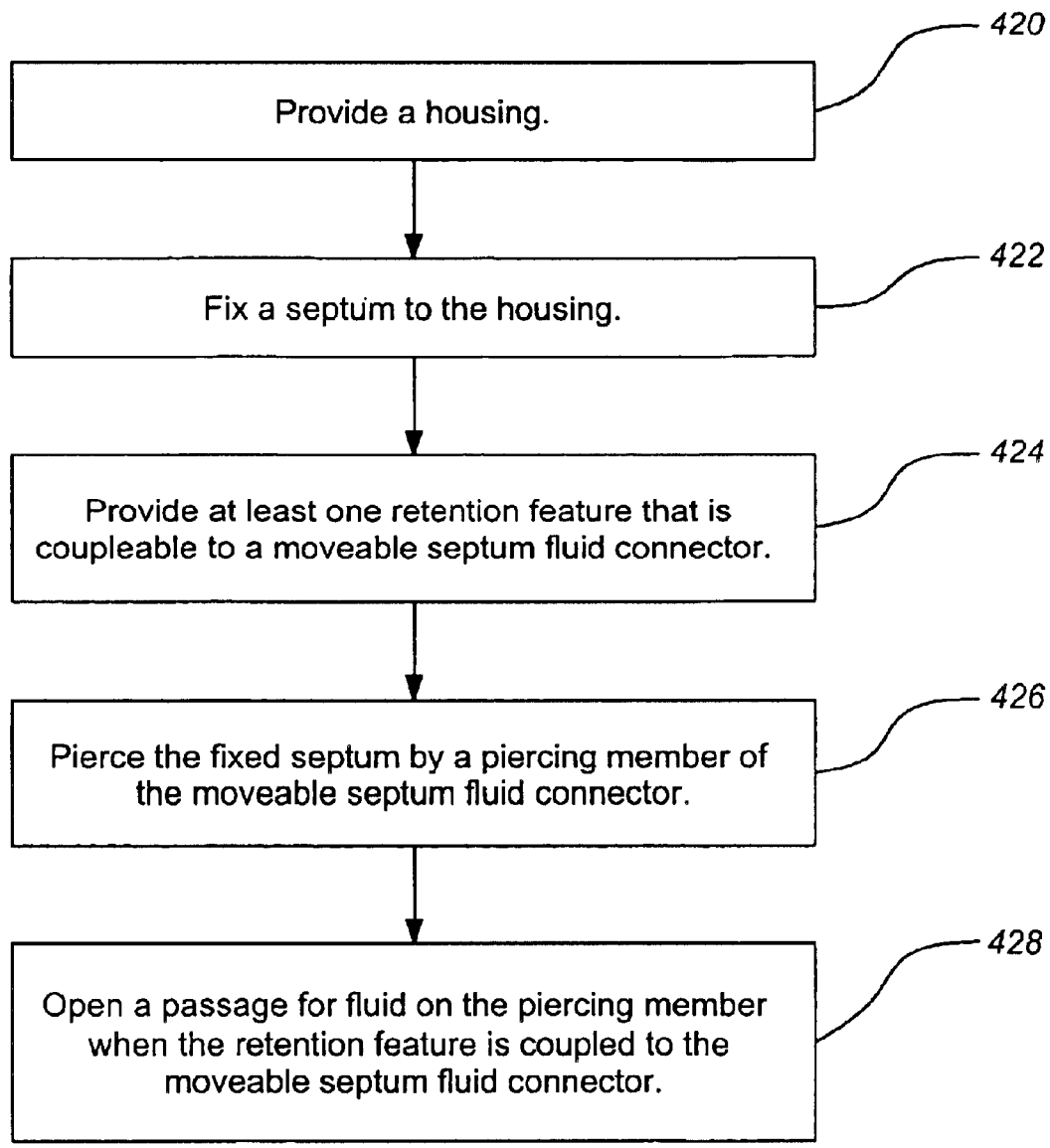

FIGS. 4A and 4B are flowcharts of exemplary methods of connecting fluid conduits. FIG. 4A is a flowchart of a method of connecting a fluid conduit where a housing is provided at block 400. At block 402, the moveable septum is slideably coupled with the housing to be alternately disposed in a first and second position. At block 404, in the first position, the moveable septum closes a passage in a piercing member for conducting fluid. At block 406, in the second position, the moveable septum is penetrated by the piercing member to open the passage.

FIG. 4A is a flowchart of a method of connecting a fluid conduit where a housing is provided at block 420. At block 422, a septum is fixed to the housing. Next, at block 424 at least one retention feature is provided that is coupleable to a moveable septum component. At block 426, the fixed septum is pierced by a piercing member of the moveable septum component. At block 428, a passage for fluid on the piercing member is opened when the retention feature is coupled to the moveable septum component.

CONCLUSION

The foregoing description including the preferred embodiment of the invention has been presented for the purposes of illustration and description. It is not intended to be exhaustive or to limit the invention to the precise form disclosed. Many equivalent modifications and variations are possible in light of the above teaching.

It is intended that the scope of the invention be limited not by this detailed description, but rather by the claims appended hereto. The above specification, examples and information provide a description of the manufacture and use of the apparatus and method of the invention. Since many embodiments of the invention can be made without departing from the scope of the invention, the invention resides in the claims hereinafter appended.

What is claimed is:

1. An apparatus, comprising:
   a housing; and
   a moveable septum slideably coupled with the housing to be disposed in at least a first and a second position;
   a fluid conduit comprising a piercing member having a passage and an opening for conducting fluid;
   at least one retention feature coupled to the moveable septum, wherein the retention feature it adapted to engage a mating retention feature of a component including fixed septum and wherein the retention feature includes a snap fitting;
   wherein the piercing member is at least partially within the moveable septum to close the opening and inhibit a fluid flow in the fluid conduit coupled to the apparatus in the first position and the movable septum is penetrated by the piercing member in the second position such that the fluid flow is not inhibited through the opening of the piercing member.

2. The apparatus of claim 1, further including a carrier for holding the moveable septum and slideably coupling with the housing.

3. The apparatus of claim 1, wherein the housing includes a stop to retain the moveable septum in slideable coupling.

4. The apparatus of claim 1, wherein the apparatus is coupleable to a component including a fixed septum such that the fixed septum is pierced by the fluid conduit when the apparatus is coupled to the fixed septum component and the moveable septum is in the second position.

5. The apparatus of claim 1, wherein the retention feature is adapted to position the moveable septum in the first position before the fixed septum component is uncoupled from the fluid conduit.

6. The apparatus of claim 1, wherein the retention feature is integral to the moveable septum.

7. The apparatus of claim 1, wherein the retention feature in disposed on a carrier for holding the moveable septum and slideably coupling with the housing.

8. The apparatus of claim 1, wherein the housing includes a housing engagement feature for coupling to the fixed septum component.

9. The apparatus of claim 1, wherein the piercing member is fixed to the housing.

10. The apparatus of claim 1, wherein the piercing member is blunted.

11. The apparatus of claim 1, wherein the passage of the piercing member includes a radial opening.

12. The apparatus of claim 1, wherein the passage of the piercing member includes an axial opening.

13. A method of connecting a fluid conduit, comprising the steps of:
   providing a housing;
   providing at least one retention feature coupled to a moveable septum, wherein the retention feature is adapted to engage a mating retention feature of a fixed septum component and wherein the retention feature includes a snap fitting;
   slideably coupling a moveable septum with the housing to be alternately disposed in at least a first and second position wherein a fluid conduit comprising a piercing member having a passage and an opening for conducting fluid has the piercing member at least partially within the moveable septum to close the opening and inhibit a fluid flow in the fluid conduit in the first position and the movable septum is penetrated by the piercing member to permit the fluid flow through the opening of the piercing member in the second position; and
   coupling the fluid conduit to the fixed septum component including a fixed septum that is pierced by the piercing member when the fixed septum component is coupled and the moveable septum is in the second position.

14. The method of claim 13, further including holding the moveable septum in a carrier and slideably coupling the moveable septum with the housing.

15. The method of claim 13, wherein the housing includes a stop to retain the moveable septum in slideable coupling.

16. The method of claim 13, wherein the retention feature is adapted to position the moveable septum in the first position before the fixed septum component is uncoupled from the fluid conduit.

17. The method of claim 13, wherein the retention feature is integral to the moveable septum.

18. The method of claim 13, wherein the retention feature is disposed on a carrier for holding the moveable septum and slideably coupling with the housing.

19. The method of claim 13, wherein the housing includes a housing engagement feature for coupling to the fixed septum component.

20. The method of claim 13, wherein the piercing member is fixed to the housing.

21. The method of claim 13, wherein the piercing member is blunted.

22. The method of claim 13, wherein the passage of the piercing member includes a radial opening.

23. The method of claim 13, wherein the passage of the piercing member includes an axial opening.

24. An apparatus, comprising:
a housing;
a septum fixed to the housing; and
at least one retention feature including a snap fitting coupleable to a moveable septum component including a fluid conduit comprising a piercing member having a passage and an opening for conducting fluid and adapted to position a moveable septum of the moveable septum component in a first position before the retention feature is uncoupled wherein the piercing member is at least partially within the moveable septum to close the opening and is alternately disposed in a first position where the moveable septum inhibits a fluid flow and a second position where the moveable septum permits the fluid flow through the opening of the piercing member;
wherein the fixed septum is pierced by the piercing member and the moveable septum is disposed in the second position when the retention feature is coupled to the moveable septum component.

25. The apparatus of claim 24, wherein the retention feature is integral to the fixed septum.

26. The apparatus of claim 24, wherein the retention feature is integral to the housing.

27. The apparatus of claim 24, wherein the housing includes a housing engagement feature to engage the moveable septum component.

28. The apparatus of claim 24, wherein the housing includes a housing engagement feature for coupling to the moveable septum component.

29. The apparatus of claim 24, wherein the piercing member is blunted.

30. The apparatus of claim 24, wherein the passage of the piercing member includes a radial opening.

31. The apparatus of claim 24, wherein the passage of the piercing member includes an axial opening.

32. A method of connecting a fluid conduit, comprising the steps of:
providing a fixed septum component having a housing, a septum fixed to the housing and at least one retention feature including a snap fitting coupleable to a moveable septum component, the movable septum component including a fluid conduit comprising a piercing member having a passage and an opening for conducting fluid wherein the piercing member is at least partially within the movable septum to close the opening and inhibit a fluid flow in the fluid conduit in a first position; and
connecting the fixed septum component with the moveable septum component;
wherein the fixed septum is pierced by the piercing member of the movable septum component to a second position permitting a fluid flow through the opening of the piercing member when the retention feature is coupled to the moveable septum component.

33. The method of claim 32, wherein the retention feature is integral to the fixed septum.

34. The method of claim 32, wherein the retention feature is integral to the housing.

35. The method of claim 32, wherein the housing includes a housing engagement feature to engage the moveable septum component.

36. The method claim 32, wherein the housing includes a housing engagement feature to coupling to moveable septum component.

37. The method of claim 32, wherein the piercing member is blunted.

38. The method of claim 32, wherein the passage of the piercing member includes a radial opening.

39. The method of claim 32, wherein the passage of the piercing member includes an axial opening.

40. The method of claim 32, wherein the retention feature is adapted to position the moveable septum in the first position before the retention feature is uncoupled.

41. A fluid coupling system, comprising
a moveable septum component, including:
a first housing;
a piercing member having a passage and an opening for conducting fluid; and
a moveable septum slideably coupled with the first housing to be alternately disposed in at least a first position where the piercing member is at least; partially within the moveable septum to close the opening and inhibit a fluid flow in the fluid conduit and a second position where the moveable septum is penetrated by the piercing member to permit the fluid flow through the opening of the piercing member; and
a fixed septum component coupleable to the moveable septum component, including:
a second housing;
an immobile septum fixed to the second housing; and
at least one retention feature coupled to the moveable septum, wherein the retention feature includes a snap fitting and is adapted to engage a mating retention feature of the fixed septum component;
wherein the fixed septum is pierced by the piercing member to permit the fluid flow when the fixed septum component and the moveable septum component are coupled with the moveable septum in the second position.

42. The system of claim 41, wherein the a moveable septum component further includes a carrier for holding the moveable septum and slideably coupling with the housing.

43. The system of claim 41, wherein the first housing includes a stop to retain the moveable septum in slideable coupling.

44. The system of claim 41, wherein the retention feature is adapted to position the moveable septum in the first position before she fixed septum component is uncoupled from the fluid conduit.

45. The system of claim 41, wherein the retention feature is integral to the moveable septum.

46. The system of claim 41, wherein the retention feature is disposed on a carrier for holding the moveable septum and slideably coupling with the first housing.

47. The system of claim 41, wherein the first housing includes a housing engagement feature for coupling to a mating housing engagement feature of the second housing.

48. The system of claim 41, wherein the piercing member is fixed to the first housing.

49. The system of claim 41, wherein the piercing member is blunted.

50. The system of claim 41, wherein the passage of the piercing member includes a radial opening.

51. The system of claim 41, wherein the passage of the piercing member includes an axial opening.

* * * * *